US009656267B2

(12) United States Patent
Fu (10) Patent No.: US 9,656,267 B2
(45) Date of Patent: May 23, 2017

(54) MAGNETIC RACK

(71) Applicant: NVIGEN, INC., Sunnyvale, CA (US)

(72) Inventor: Aihua Fu, Sunnyvale, CA (US)

(73) Assignee: NVIGEN, INC., Sunnyvale, CA (US)

( * ) Notice: Subject to any disclaimer, the term of this patent is extended or adjusted under 35 U.S.C. 154(b) by 0 days.

(21) Appl. No.: 14/857,789

(22) Filed: Sep. 17, 2015

(65) Prior Publication Data

US 2017/0080430 A1   Mar. 23, 2017

(51) Int. Cl.
| | |
|---|---|
| *B01L 9/06* | (2006.01) |
| *B03C 1/02* | (2006.01) |
| *G01N 1/40* | (2006.01) |
| *B01L 9/00* | (2006.01) |

(52) U.S. Cl.
CPC ............... *B01L 9/06* (2013.01); *B01L 9/523* (2013.01); *B03C 1/02* (2013.01); *G01N 1/4077* (2013.01); *B01L 2200/02* (2013.01); *B01L 2300/0809* (2013.01); *B01L 2300/0848* (2013.01); *B01L 2300/12* (2013.01); *G01N 2001/4038* (2013.01)

(58) Field of Classification Search
CPC ....... B03C 1/00; B03C 2201/20; B03C 1/288; B03C 2201/22; B01L 9/06; B01L 9/065; B01L 2200/0668; B01L 2400/043
See application file for complete search history.

(56) References Cited

U.S. PATENT DOCUMENTS

| | | | | |
|---|---|---|---|---|
| 4,895,650 | A * | 1/1990 | Wang | B01L 9/06 210/222 |
| 5,186,827 | A * | 2/1993 | Liberti | A23L 3/32 210/222 |
| 5,541,072 | A * | 7/1996 | Wang | B03C 1/01 209/214 |
| 5,571,481 | A * | 11/1996 | Powell | B01L 9/06 209/215 |
| 5,779,907 | A * | 7/1998 | Yu | B01L 3/5085 210/222 |
| 6,040,192 | A * | 3/2000 | Tuunanen | B01L 3/02 209/217 |
| 6,514,416 | B1 * | 2/2003 | Harradine | G01N 33/54333 210/222 |
| 6,805,840 | B1 * | 10/2004 | Tajima | B01L 3/0231 210/695 |
| 7,267,800 | B2 * | 9/2007 | Takii | G01N 35/10 422/501 |
| 7,927,495 | B2 * | 4/2011 | Lutze | B03C 1/286 210/222 |
| 8,088,285 | B2 * | 1/2012 | Siddiqi | B01F 13/0809 209/217 |
| 8,251,221 | B1 * | 8/2012 | Castaneda | B65D 81/02 206/446 |

(Continued)

*Primary Examiner* — Brian R Gordon
(74) *Attorney, Agent, or Firm* — Jun He Law Offices P.C.; James J. Zhu (57) ABSTRACT

A magnetic rack includes a bottom plate; a top plate mounted onto the bottom plate, the top plate having therein a first plurality of tube holes for retaining one or more tubes, each tube hole having an opening and a supporting wall extending from the opening between the top plate and the bottom plate; and a second plurality of magnetic assemblies distributed between at least a portion of the first plurality of tube holes, each magnetic assembly being configured to produce a magnetic field in one or more tube holes adjacent thereto.

17 Claims, 6 Drawing Sheets

(56) References Cited

U.S. PATENT DOCUMENTS

| | | | |
|---|---|---|---|
| 2002/0098121 A1* | 7/2002 | Astle | B01L 9/523 422/527 |
| 2006/0038648 A1* | 2/2006 | Humphries | B03C 1/0332 335/306 |
| 2007/0221543 A1* | 9/2007 | Karmeniemi | B03C 1/0332 209/223.1 |
| 2008/0156714 A1* | 7/2008 | Su | B03C 1/288 210/222 |
| 2009/0064800 A1* | 3/2009 | Fasching | B01L 9/523 73/863.21 |
| 2009/0324451 A1* | 12/2009 | Yin | B01L 9/523 422/400 |
| 2010/0284864 A1* | 11/2010 | Holenstein | B01L 3/5085 422/511 |
| 2011/0203997 A1* | 8/2011 | Meyer | B03C 1/288 210/695 |
| 2013/0273552 A1* | 10/2013 | Ohashi | B01L 3/5025 435/6.12 |
| 2013/0315800 A1* | 11/2013 | Yin | B01L 9/523 422/552 |
| 2014/0024136 A1* | 1/2014 | Chappell | G01N 35/0098 436/501 |
| 2014/0140804 A1* | 5/2014 | Focke | B01L 9/06 414/801 |
| 2015/0119274 A1* | 4/2015 | Piletsky | B01L 3/5085 506/9 |

* cited by examiner

MAGNETIC RACK

FIELD OF THE INVENTION

The present application relates to a magnetic rack for separating magnetic particles from a non-magnetic medium contained within sample tubes.

BACKGROUND OF THE INVENTION

Magnetic field can be used to separate magnetic particles from a non-magnetic medium such as a suspension, which has a wide application in chemistry, biochemistry or medical sciences. Specifically, a rack-like arrangement is convenient for simultaneously processing a number of samples contained in respective sample tubes.

Various magnetic racks with magnets disposed therein have been developed. The magnets may be positioned in a row along a lengthwise direction of the magnetic rack to produce the magnetic field. When a sample tube is inserted into the magnetic rack and approaches the magnets, the magnetic field can affect the suspended magnetic particles that are dispersed within the suspension in the sample tube, attracting the particles using magnetic force. The particles will then be collected and concentrated along the sidewall of the sample tube. However, the conventional magnetic racks are not fit for insertion of sample tube strips.

Thus, there is a continued need to improve the magnetic rack design.

SUMMARY OF THE INVENTION

An objective of the present application is to provide a magnetic rack suitable for insertion of sample tube strips.

In an aspect of the application, there is disclosed a magnetic rack. The magnetic rack comprises a bottom plate; a top plate mounted onto the bottom plate, the top plate having therein a first plurality of tube holes for retaining one or more tubes, each tube hole having an opening and a supporting wall extending from the opening to between the top plate and the bottom plate; and a second plurality of magnetic assemblies distributed between at least a portion of the first plurality of tube holes, each magnetic assembly being configured to produce a magnetic field in one or more tube holes adjacent thereto.

In another aspect of the application, there is also disclosed a magnetic rack. The magnetic rack comprises a bottom plate; a top plate mounted onto the bottom plate, the top plate having therein a plurality of tube holes for retaining one or more tubes and arranged in a rectangular array, each tube hole having an opening and a supporting wall extending from the opening between the top plate and the bottom plate; wherein each four adjacent tube holes of the plurality of tube holes has at their center a magnetic assembly for producing a magnetic field in the four adjacent tube holes.

The foregoing has outlined, rather broadly, features of the present application. Additional features of the present application will be described, hereinafter, which form the subject of the claims of the present application. It should be appreciated by those skilled in the art that the conception and specific embodiments disclosed herein may be readily utilized as a basis for modifying or designing other structures or processes for carrying out the objectives of the present application. It should also be realized by those skilled in the art that such equivalent constructions do not depart from the spirit and scope of the present application as set forth in the appended claims.

BRIEF DESCRIPTION OF DRAWINGS

The aforementioned features and other features of the present application will be further described in the following paragraphs by referring to the accompanying drawings and the appended claims. It will be understood that, these accompanying drawings merely illustrate certain embodiments in accordance with the present application and should not be considered as limitation to the scope of the present application. Unless otherwise specified, the accompanying drawings need not be proportional, and similar reference characters generally denote similar elements.

DETAILED DESCRIPTION OF THE EMBODIMENTS

The following detailed description refers to the accompanying drawings as a part of the present application. The illustrative embodiments described in the detailed description, the accompanying drawings and the claims are not limiting, and other embodiments may be adopted, or modifications may be made without deviating from the spirit and subject of the present application. It should be understood that the various aspects of the present application described and graphically presented herein may be arranged, replaced, combined, divided and designed in many different configurations, and these different configurations are implicitly comprised in the present application.

Figure 1:
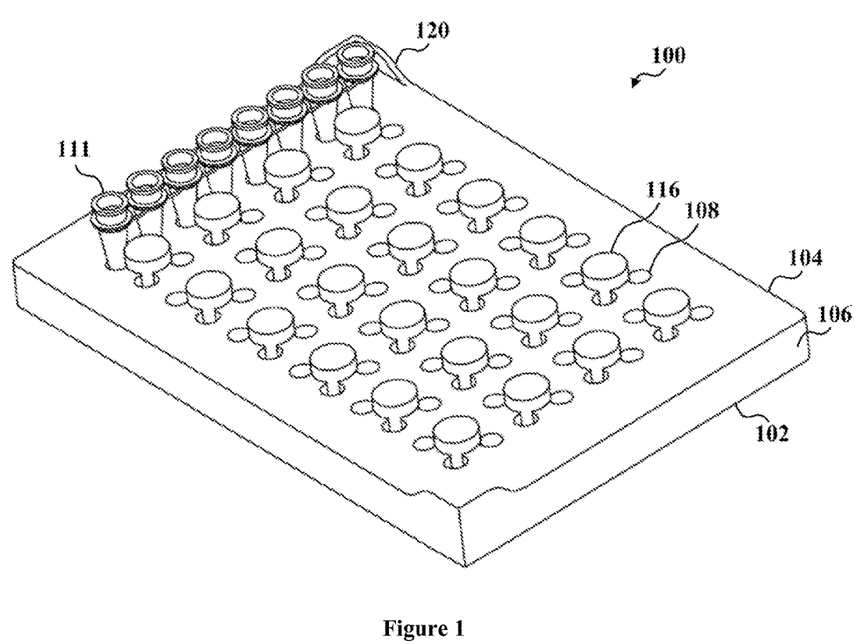
FIG. 1 shows a perspective view of a magnetic rack 100 according to an embodiment of the present application.
Figure 2:
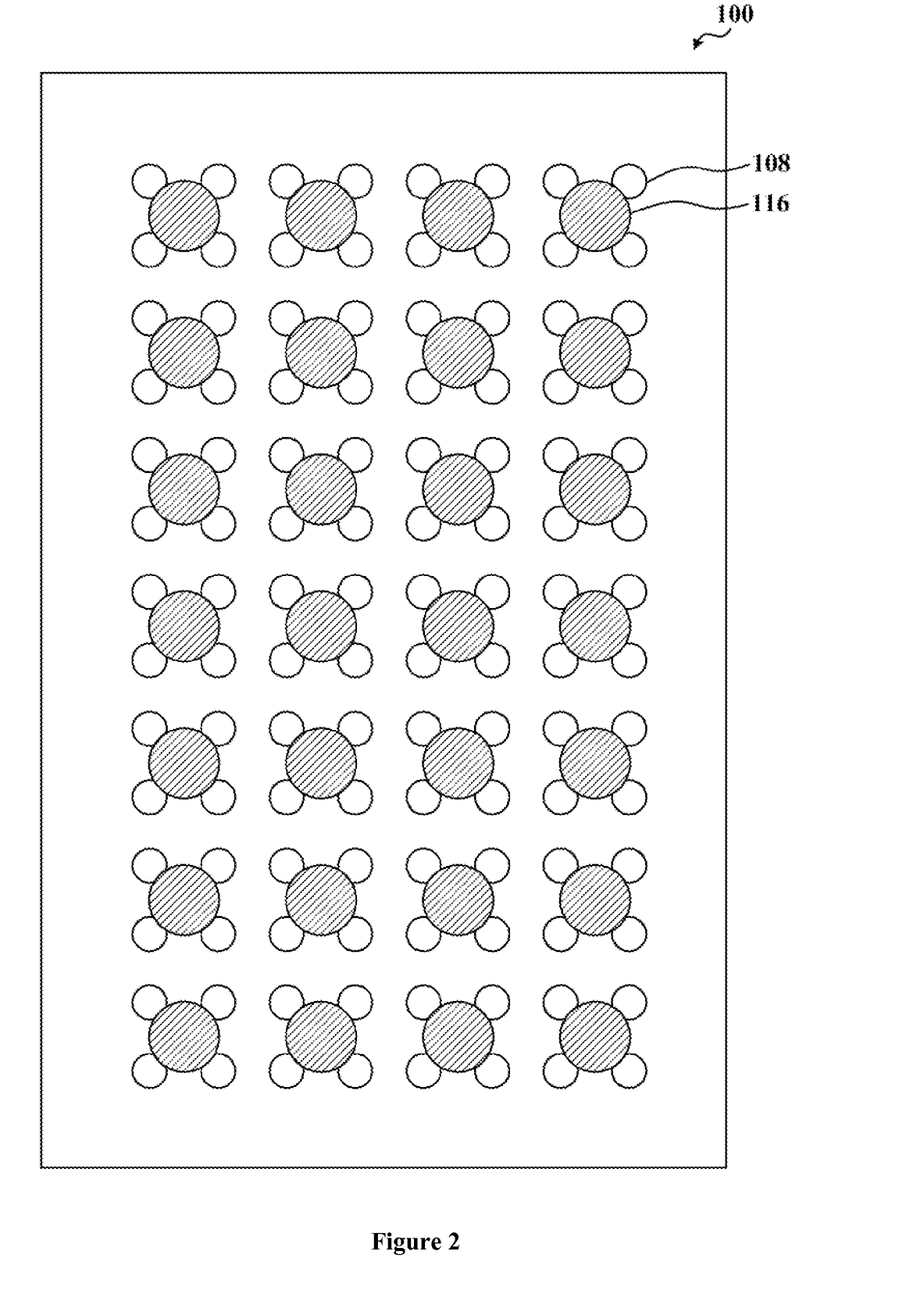
FIG. 2 shows a top view of the magnetic rack 100 in FIG. 1.
Figure 3:
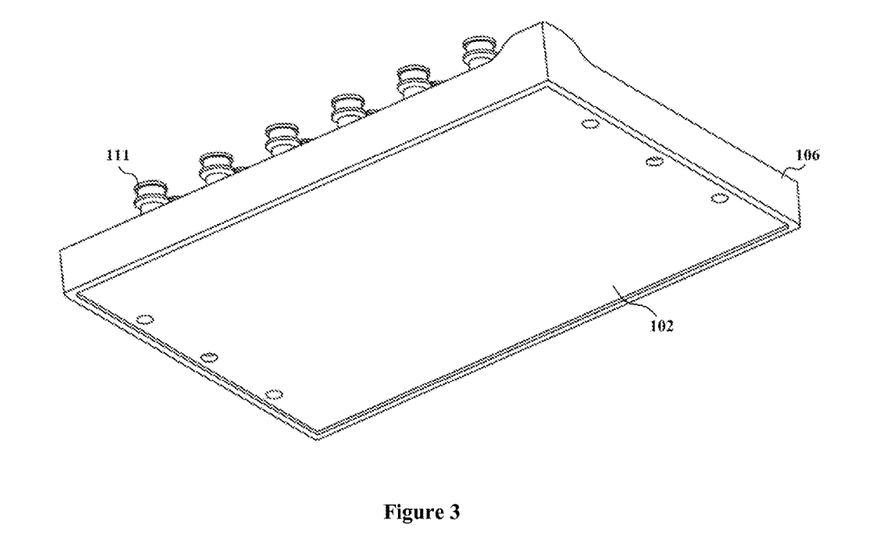
FIG. 3 shows a bottom view of the magnetic rack 100 in FIG. 1.
Figure 4:
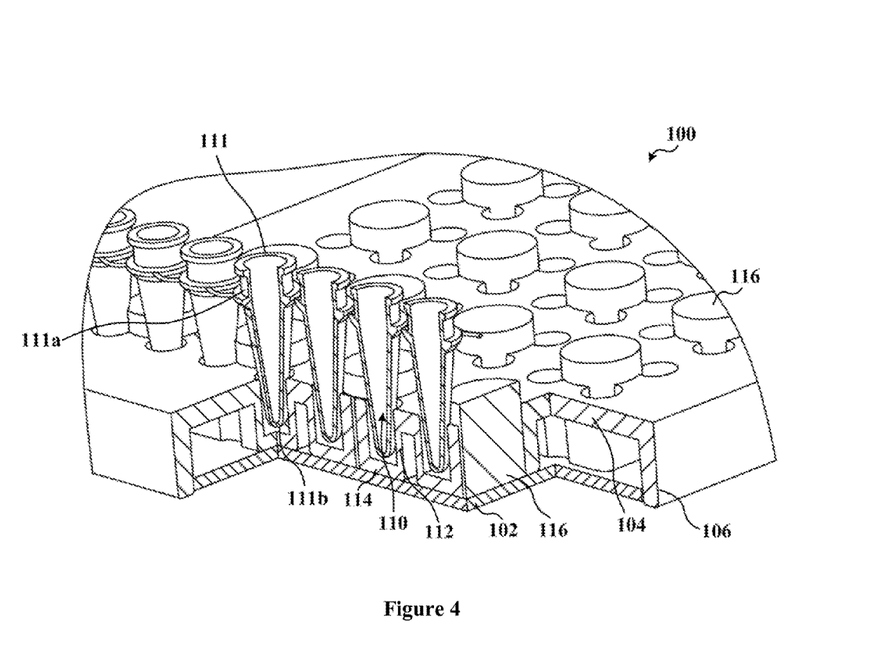
FIG. 4 shows a cross-sectional view of the magnetic rack 100 in FIG. 1.

FIGS. 1 to 4 show a magnetic rack 100 according to an embodiment of the present application. FIG. 1 shows a perspective view of the magnetic rack 100, FIG. 2 shows a top view of the magnetic rack 100, FIG. 3 shows a bottom view of the magnetic rack 100, and FIG. 4 shows a cross-sectional view of the magnetic rack 100. The magnetic rack 100 can be used to retain sample tubes, sample tube strips or multiwell plates.

As shown in FIGS. 1 to 4, the magnetic rack 100 includes a bottom plate 102, which is made of magnetic shielding material such as steel, permalloy or the like, for example. A top plate 104 is mounted onto the bottom plate 102 such that the bottom plate 102 and top plate 104 forms a housing of the magnetic rack 100. A peripheral wall 106 of the top plate 104 extends downward from a topside of the top plate 104 to the bottom plate 102, thereby connecting the two plates together as a cubic box, as well as enclosing certain parts of the magnetic rack 100 inside the housing. In certain embodiments, the top plate 104 may be made of plastics or the like, which is easy to mold.

The top plate 104 has therein a first plurality of tube holes 108. Each tube hole 108 is fit for retaining a sample tube such as a PCR (polymerase chain reaction) tube. Referring to FIG. 4, each tube hole 108 has an opening 110 and a supporting wall 112 extending from the opening 110 to between the top plate 104 and the bottom plate 102. A sample tube 111 may have a substantially cylindrical or tapered sidewall 111a with a closed bottom 111b, which may be flat, U-shaped or V-shaped. When the sample tube 111 is inserted into the tube hole 108 through its opening 110, its sidewall 111a and/or closed bottom 111b may be in contact with the supporting wall 112 such that it can stand stably within the tube hole 108. In the embodiment shown in FIG. 4, the supporting wall 112 has a closed bottom 114 seated on the bottom plate 102. In other words, the supporting wall 112 may extend over substantially an entire height of the peripheral wall 106 of the top plate 104. Alternatively, the supporting wall 112 may not extend over the entire height of the peripheral wall 106 of the top plate 104, and the closed bottom 114 of the tube hole 108 may be over but not in contact with the bottom plate 102. In some other embodiments, the supporting wall may have an open bottom with a reduced or same diameter compared with that of the opening. Moreover, the supporting wall may be dissected vertically into several sections, thereby the supporting wall may have certain flexibility allowing the diameter of the tube hole, which is defined by the supporting wall, slightly expand depending on the sample tube inserted thereinto. The flexibility of the supporting wall ensures that the sample tubes can be firmly retained within the tube holes.

The magnetic rack 100 further includes a second plurality of magnetic assemblies 116 distributed between at least a portion of the first plurality of tube holes 108. Each magnetic assembly 116 produces a magnetic field in one or more tubes holes 108 adjacent thereto. When the sample tubes 111 are inserted into the respective tube holes 108, magnetic particles and associated bio-molecules contained in the sample tubes 111 can be attracted into a tight magnetic pellet onto the sidewall or bottom of the sample tube 111. In certain embodiments, the magnetic assemblies 116 may be configured such that the magnetic pellets in the sample tubes 111 retained in the magnetic rack 100, i.e. retained in the tube holes 108, are pulled down to the sidewall of the sample tubes 111 but above the bottom of the sample tubes 111. For example, a lower end of the magnetic assembly 116 may be above the bottom of the adjacent sample tube 111. In this way, the magnetic rack 100 may collect the magnetic pellets to the sidewall of the sample tube 111, leaving the bottom of the sample tube free of magnetic pellets. Thus, it is convenient to completely remove supernatant in the sample tubes by using a pipette or other utensils since its tip could touch the bottom of the sample tubes to suck out more completely the solutions.

The magnetic field distribution produced by the magnetic assemblies 116 may be configured by properly positioning the magnetic assemblies 116 close to the tube holes 108. For example, as shown in FIG. 4, the tube holes 108 is of a height identical to that of the top plate 104, and the magnetic assemblies 116, which is a cylindrical magnet, is of a height greater than that of the top plate 104 as it partially extend over the topside of the top plate 104. In some other embodiments, the magnetic assemblies 116 may not extend onto the bottom plate 102, or may not extend above the topside of the top plate 104.

Referring to FIGS. 1 and 2, the first plurality of tube holes 108 are arranged in a rectangular array, or particularly an 8×12 array, when viewed from top of the magnetic rack 100. The tube holes 108 are spaced apart from each other with spacing the same as that of a sample tube strip such as an 8-tube strip, a 12-tube strip, or that of a multiwell plate such as a 96-well plate, a 48-well plate, a 24-well plate or a 12-well plate, which is to be retained by the magnetic rack 100. The tube strip may have tubes with closed bottoms such as flat bottoms, U-shaped bottoms or V-shaped bottoms, and similarly, the multiwell plate may have wells with V-shaped, U-shaped or flat bottoms. Moreover, several strips can be retained by the magnetic rack 100 at the same time. Individual sample tubes may also be retained within the tube holes 108 separately. It will be readily appreciated that the spacing and the size of the tube holes array may be designed according to industrial standards in this art. For example, a distance between centers of two neighboring tube holes may be 9.0 mm for the 96-well plate, or 4.5 mm for a 392-well plate. Also, the tube holes can be sized to match with the outer diameter of the sidewalls or bottoms of the tubes or wells to be received, thereby permitting the insertion of the tubes or wells.

The top plate 104 further has a positioning member 120 for positioning the 96-well plate or other multiwell plates when the multiwell plate is supported on the magnetic rack 100 with its wells or tubes retained within the tube holes 108. In certain embodiments, the positioning member 120 may include two protruding walls encircling two respective corners of the top plate 104 respectively and arranged along a diagonal line of the top plate 104. Each protruding wall is L-shaped. In some other embodiments, the positioning member may include four protruding walls encircling all four corners of the top plate, respectively. In some other embodiments, the positioning member may include several flat protruding walls around the periphery of the topside of the top plate 104.

The second plurality of magnetic assemblies 116 may also be arranged in a rectangular array, similar to the tube hole array. In the embodiment shown in FIGS. 1 and 2, each magnetic assembly 116 includes a cylindrical magnet. In particular, each magnetic assembly 116 may be positioned at a center of four adjacent tube holes 108, such that the array of magnetic assemblies 116 may have 24 magnetic assemblies 116 for the array of 96 tube holes shown in FIGS. 1 and 2. In certain embodiments, each tube hole 108 may overlap with a magnetic assembly 116 adjacent thereto such that at least a portion of the adjacent magnetic assembly 116 protrudes into the tube hole 108 through its supporting wall 112. In this way, the magnetic assembly 116 can be in direct contact with the adjacent tube holes 108 to increase the strength of the magnetic field in the tube holes 108. In some other embodiments, the tube holes 108 may not overlap with the magnetic assemblies 116. For example, the supporting walls of the tube holes 108 may be substantially tangent with outer surfaces of the magnetic assemblies 116, respectively. Moreover, the magnetic assembly 116 positioned at the center of four adjacent tube holes 108 may produce magnetic fields with the same strength in the four adjacent tube holes 108. For example, distances from the center of the cylindrical magnet 116 to the centers of the four adjacent tube holes 108 may be equal to each other.

Still referring to FIGS. 1 and 3, the top plate 104 has the peripheral wall connecting the bottom plate 102 with the top plate 104. In particular, an edge of the bottom plate 102 is enclosed by the peripheral wall of the top plate 104. Moreover, the bottom plate 104 may be attached to the peripheral wall of the top plate 104 by adhesion or screw or rivet connection. Such separately formed structure is easy to manufacture and low in cost.

Figure 5:
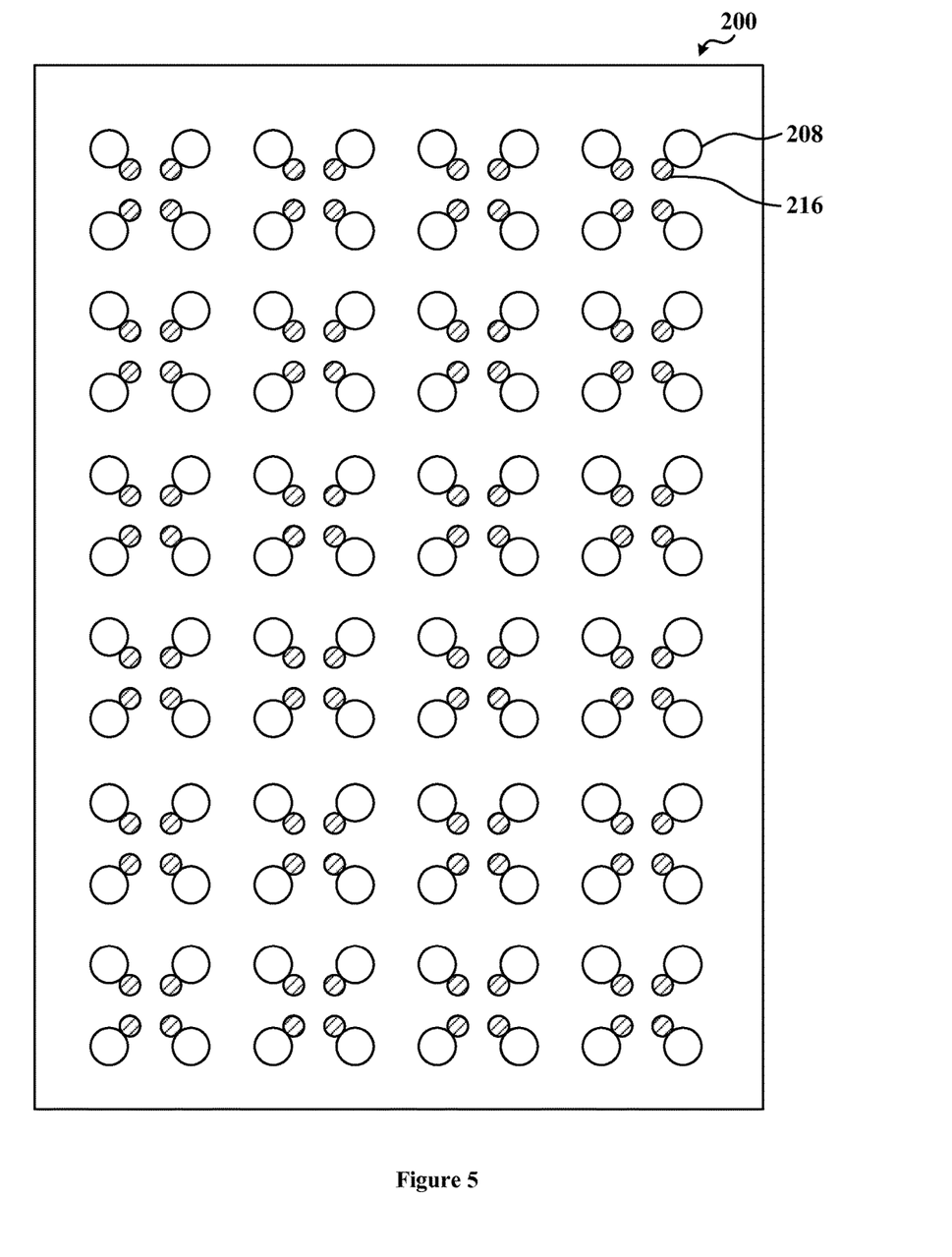
FIG. 5 shows a top view of a magnetic rack 200 according to another embodiment of the present application.

In some other embodiments, each magnetic assembly may have multiple magnets. FIG. 5 shows a magnetic rack 200 according to an embodiment of the application. As shown in FIG. 5, the magnetic rack 200 include twenty four magnetic assemblies 216 positioned between four adjacent tube holes 208 and each including four cylindrical magnets. Moreover, each of the four cylindrical magnets of a magnetic assembly 216 is adjacent to a tube hole 208 to produce a magnetic field therein.

Figure 6:
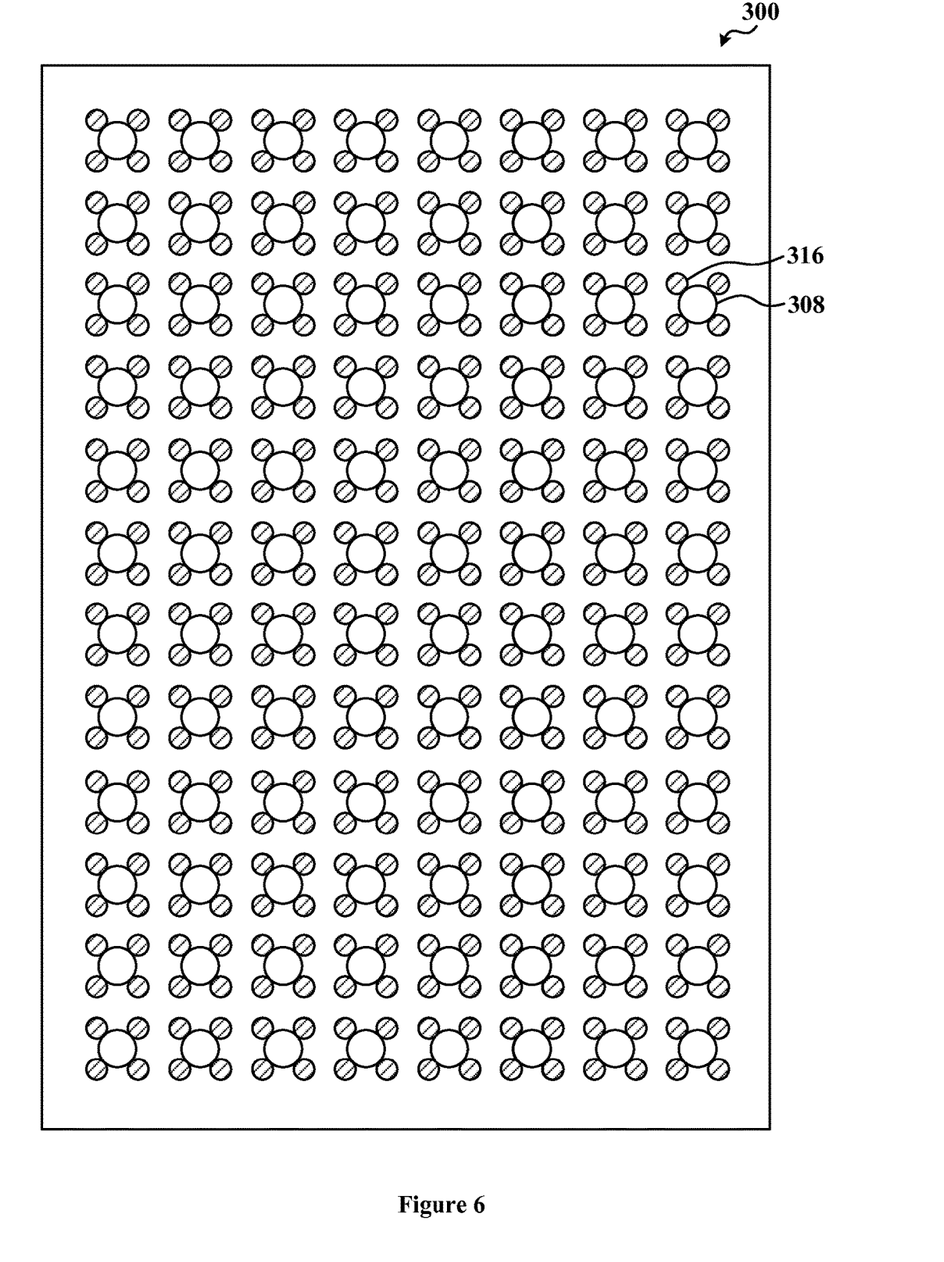
FIG. 6 shows a top view of a magnetic rack 300 according to yet another embodiment of the present application.

In the embodiments shown in FIGS. 2 and 5, each tube hole is adjacent to only one magnetic assembly. In some other embodiments, each tube hole may be adjacent to multiple magnetic assemblies. FIG. 6 shows a magnetic rack 300 according to an embodiment of the application. As shown in FIG. 6, each tube hole 308 is surrounded by four magnetic assemblies 316, and each magnetic assembly 316 include four magnets. The magnetic assemblies 316 surrounding the tube hole 308 produces substantially over an entire circumference of the tube hole 308 a magnetic field with an increased strength compared with the magnetic rack 200 of FIG. 5.

Figure 7:
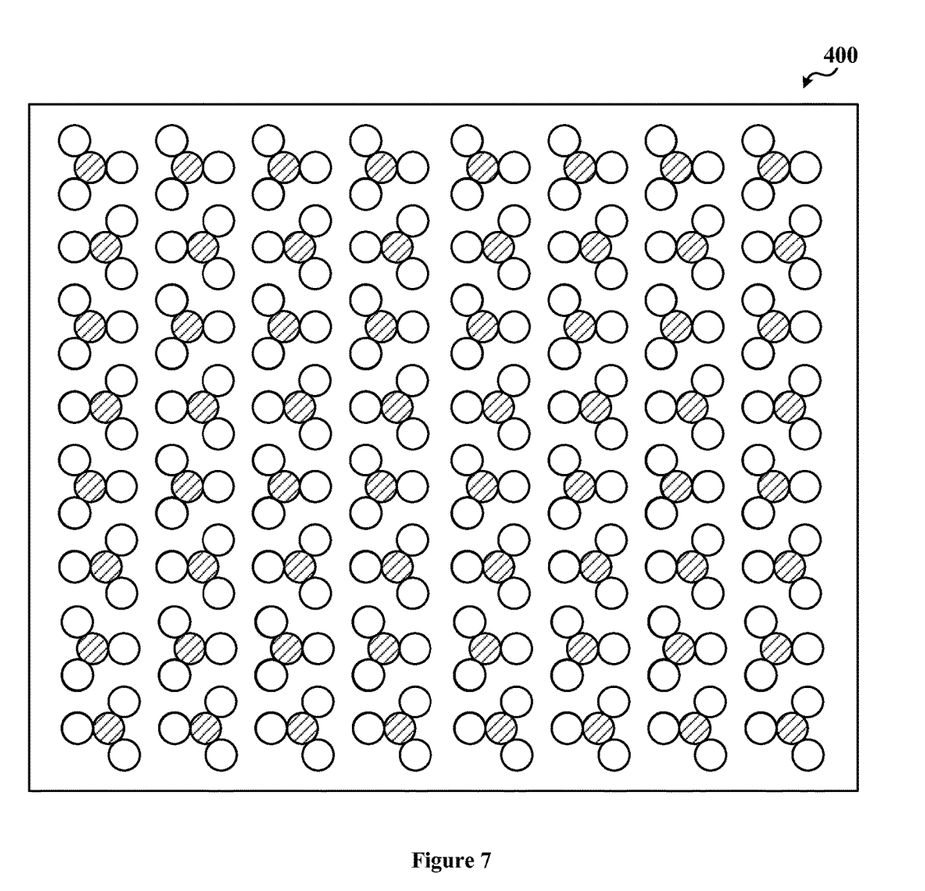
FIG. 7 shows a top view of a magnetic rack 400 according to a further embodiment of the present application.

In some other embodiments, the tube holes of the magnetic rack may be arranged in a non-rectangular array. FIG. 7 shows a magnetic rack 400 according to an embodiment of the application. As shown in FIG. 7, the magnetic rack 400 includes a tube hole array. Every three adjacent tube holes are arranged in a regular triangular manner, with a magnetic assembly, which is a cylindrical magnet, positioned at their center. The non-rectangular array of tube holes can be used to retain sample tube strips or individual sample tubes. It will readily appreciated by a person skilled in the art that the arrangement of the tube holes of the magnetic rack may be designed to fit for various types of sample tube strips or plates.

It should be noted that, although several modules or sub-modules of the magnetic rack have been described in the previous paragraphs, such division is exemplary and not mandatory. Practically, according to the embodiments of the present application, the functions and features of two or more modules described above may be embodied in one module. On the other hand, the function and feature of any one module described above may be embodied in two or more modules.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope. The scope and spirit of the present application is defined by the appended claims.

What is claimed is:

1. A magnetic rack, comprising:
   a bottom plate;
   a top plate mounted onto the bottom plate, the top plate having therein a first plurality of tube holes for retaining one or more tubes, each tube hole having an opening and a supporting wall extending from the opening between the top plate and the bottom plate; and
   a second plurality of magnetic assemblies distributed between at least a portion of the first plurality of tube holes, each magnetic assembly being configured to produce a magnetic field in one or more tube holes adjacent thereto to the magnetic assembly;
   wherein each tube hole partially overlaps with a magnetic assembly adjacent to the tube hole such that a portion of the adjacent magnetic assembly protrudes into the tube hole through the supporting wall of the tube hole.

2. The magnetic rack of claim 1, wherein each magnetic assembly comprises a cylindrical magnet.

3. The magnetic rack of claim 1, wherein both the first plurality of tube holes and the second plurality of magnetic assemblies are arranged in rectangular arrays, and each magnetic assembly is positioned at a center of a group of four tube holes of the first plurality of tube holes, and wherein the group of four tube holes are adjacent to the magnetic assembly.

4. The magnetic rack of claim 3, wherein each tube hole is adjacent to a magnetic assembly.

5. The magnetic rack of claim 1, wherein the second plurality of magnetic assemblies are positioned such that the respective magnetic fields produced in each of the respective first plurality of tube holes are of the same strength.

6. The magnetic rack of claim 1, wherein the top plate is made of plastics.

7. The magnetic rack of claim 1, wherein the bottom plate is made of magnetic shielding material.

8. The magnetic rack of claim 1, wherein the top plate has a peripheral wall for connecting the bottom plate with the top plate, and an edge of the bottom plate is enclosed by the peripheral wall of the top plate.

9. The magnetic rack of claim 1, wherein the top plate is of a rectangular shape adapted for supporting a multiwell plate with multiple wells, and wherein the top plate has a positioning member for positioning the multiwell plate, and the positioning member is such configured that the wells of the multiwell plate can be retained in the first plurality of tube holes when the multiwell plate is supported on the magnetic rack.

10. The magnetic rack of claim 9, wherein the positioning member comprises two protruding walls encircling two respective corners of the top plate and arranged along a diagonal line of the top plate.

11. The magnetic rack of claim 1, wherein the second plurality of magnetic assemblies are seated onto the bottom plate and at least extend between the bottom plate and the top plate.

12. A magnetic rack, comprising:
    a bottom plate; and
    a top plate mounted onto the bottom plate, the top plate having therein a plurality of tube holes for retaining one or more tubes and arranged in a rectangular array, each tube hole having an opening and a supporting wall extending from the opening between the top plate and the bottom plate;
    wherein each four adjacent tube holes of the plurality of tube holes forms a group, and the group of four adjacent tube holes has at its center a magnetic assembly for producing a magnetic field in the group of four adjacent tube holes;
    wherein each tube hole overlaps with a magnetic assembly adjacent to the tube hole such that at least a portion of the adjacent magnetic assembly protrudes into the tube hole through the supporting wall of the tube hole.

13. The magnetic rack of claim 12, wherein each magnetic assembly comprises a cylindrical magnet.

14. The magnetic rack of claim 12, wherein the magnetic assemblies are attached to the bottom plate and at least extend between the bottom plate and the top plate.

15. The magnetic rack of claim 12, wherein the top plate is of a rectangular shape adapted for supporting a multiwell plate with multiple wells, and wherein the top plate has a positioning member for positioning the multiwell plate, and the positioning member is such configured that the wells of the multiwell plate can be retained in the first plurality of tube holes when the multiwell plate is supported on the magnetic rack.

16. The magnetic rack of claim 12, wherein the top plate has a peripheral wall for connecting the bottom plate with the top plate, and an edge of the bottom plate is enclosed by the peripheral wall of the top plate.

17. The magnetic rack of claim 12, wherein the top plate is made of plastics and the bottom plate is made of steel.

* * * * *